US010828361B2

(12) United States Patent
Danzig

(10) Patent No.: US 10,828,361 B2
(45) Date of Patent: *Nov. 10, 2020

(54) REGIMENS FOR IMMUNISATION WITH MENINGOCOCCAL CONJUGATES

(75) Inventor: Lisa Danzig, San Francisco, CA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 317 days.

This patent is subject to a terminal disclaimer.

(21) Appl. No.: 12/287,225

(22) Filed: Oct. 6, 2008

(65) Prior Publication Data

US 2009/0098156 A1 Apr. 16, 2009

Related U.S. Application Data

(63) Continuation-in-part of application No. 12/225,501, filed as application No. PCT/US2007/007115 on Mar. 22, 2007, now Pat. No. 10,543,265.

(60) Provisional application No. 60/785,234, filed on Mar. 22, 2006, provisional application No. 60/997,781, filed on Oct. 4, 2007.

(51) Int. Cl.
 *A61K 39/095* (2006.01)
 *A61K 39/00* (2006.01)

(52) U.S. Cl.
 CPC ...... *A61K 39/095* (2013.01); *A61K 2039/545* (2013.01); *A61K 2039/55* (2013.01); *Y02A 50/466* (2018.01)

(58) Field of Classification Search
 CPC ........ A61K 2039/6037; A61K 2039/70; A61K 39/095; A61K 2039/55505; A61K 39/116; A61K 47/646; A61K 39/39; A61K 47/02; A61K 47/08; A61K 47/24; A61K 47/61; A61K 47/64; A61K 47/6415; A61K 2039/627; A61K 2039/54; A61K 2039/545; A61K 2039/575; A61K 2039/62; A61K 39/0017; A61K 39/0018; A61K 39/05; A61K 39/08; A61K 39/092; A61K 39/099; A61K 39/102; A61K 39/12; A61K 39/292; A61K 39/385; A61K 9/0019; A61K 47/4833; C07K 14/22
 USPC ...................... 424/197.11, 250.1, 831; 514/2; 536/123.1
 See application file for complete search history.

(56) References Cited

U.S. PATENT DOCUMENTS

| | | | |
|---|---|---|---|
| 5,811,102 A | 9/1998 | Jennings et al. | |
| 6,146,902 A | 11/2000 | McMaster | |
| 6,531,131 B1 | 3/2003 | Gu et al. | |
| 6,632,437 B1 | 10/2003 | Schneerson et al. | |
| 2003/0068336 A1 | 4/2003 | Ryall | |
| 2005/0002957 A1 * | 1/2005 | Ryall | 424/190.1 |
| 2005/0106181 A1 | 5/2005 | Constantino | |
| 2007/0020293 A1 * | 1/2007 | Michon | A61K 39/095 424/236.1 |
| 2007/0082014 A1 | 4/2007 | Costantino | |
| 2008/0193476 A1 * | 8/2008 | Biemans et al. | 424/197.11 |
| 2009/0117148 A1 | 5/2009 | Costantino | |
| 2009/0297553 A1 | 12/2009 | Danzig | |

FOREIGN PATENT DOCUMENTS

| | | |
|---|---|---|
| WO | 87/06838 | 11/1987 |
| WO | 92/16232 | 10/1992 |
| WO | 96/40242 | 12/1996 |
| WO | 97/00697 | 1/1997 |
| WO | 98/30239 | 7/1998 |
| WO | 98/45312 | 10/1998 |
| WO | 98/47530 | 10/1998 |
| WO | 98/58670 | 12/1998 |
| WO | 99/18121 | 4/1999 |
| WO | 99/32653 | 7/1999 |
| WO | 00/38711 | 7/2000 |
| WO | 00/56360 | 9/2000 |
| WO | 01/30390 | 5/2001 |
| WO | 01/41800 | 6/2001 |
| WO | 2002/080965 A2 | 10/2002 |
| WO | WO 03/007985 * | 1/2003 |
| WO | WO-2003/007985 A2 | 1/2003 |
| WO | 2004/067030 A2 | 8/2004 |
| WO | WO-2004067033 | 8/2004 |
| WO | 2005/000345 | 1/2005 |
| WO | 2005/105141 A2 | 11/2005 |
| WO | 20061026689 A2 | 3/2006 |
| WO | WO 2006024946 A2 * | 3/2006 |
| WO | 2007/026249 A2 | 3/2007 |

OTHER PUBLICATIONS

Habermehl et al. In: Program and Abstract Book, 15th International Pathogenic Neisseria Conference, Queensland, Australia, p. 105, #P8.1.07, Sep. 10-15, 2006.*
Rennels et al. The Pediatr. Infect. Dis. J. 23: 429-435, 2004.*
Granoff et al. Int. J. Infect. Dis. 1: 152-157, 1997.*
Keyserling et al. Acta Pediatr. Adolesc. Med. 159: 907-913, Oct. 1, 2005.*
Peltola et al. Pediatrics 76: 91-96, 1985, abstract.*
Lepow, GR et al., Reactogenicity and Immunogenicity of a Quadrivalent Combined Meningococcal Polysaccharide Vaccine in Children, J. Infect. Dis. 154(6):1033-1036 (1986).
MacDonald, NE et al., Induction of Immunologic Memory by Conjugated vs Plain Meningococcal C Polysaccharide Vaccine in Toddlers: A Randomized Controlled Trial, JAMA 280(19):1685-1689 (1998) (doi:10.1001/jama.280.19.1685).
Goldblatt, D, Recent developments in bacterial conjugate vaccines, J. Med. Microbiol. 47:563-567 (1998).

(Continued)

*Primary Examiner* — Sarvamangala Devi
(74) *Attorney, Agent, or Firm* — Birch, Stewart, Kolasch & Birch, LLP

(57) ABSTRACT

Multivalent meningococcal conjugate vaccines are administered according to a schedule in which at least one or two doses are administered to a patient aged between 0 and 12 months, and a further dose is administered to a patient aged between 12 and 24 months.

6 Claims, No Drawings

(56) References Cited

OTHER PUBLICATIONS

Borrow, R. et al., Induction of immunological memory in UK infants by a meningococcal A/C conjugate vaccine, Epidemiol. Infect. 124:427-432 (2000).
Perkins, BA, New Opportunities for Prevention of Meningococcal Disease, JAMA. 283(21):2842-2844 (2000) (doi:10.1001/jama.283. 21.2842).
Morley, SL and Pollard, AJ, Vaccine prevention of meningococcal disease, coming soon?, Vaccine 20: 666-687 (2002).
Lingappa, JR et al., Surveillance for meningococcal disease and strategies for use of conjugate meningococcal vaccines in the United States, Vaccine 19:4566-4575 (2001).
Lindberg, AA, Glycoprotein conjugate vaccines, Vaccine 17:S28-S36 (1999).
Lieberman, JM et al., Safety and Immunogenicity of a Serogroups A/C Neisseria meningitidis Oligosaccharide-Protein Conjugate Vaccine in Young Children: A Randomized Controlled Trial, JAMA 275:1499-1503 (1996).
Levine, OS et al., Cost-effectiveness analysis for routine immunization with a quadrivalent meningococcal polysaccharide (A,C,Y,W-135)-protein conjugate vaccine in the United States, Conjugate and Polysaccharide Vaccines Poster 74 (IPNC 1996).
Fusco, PC et al., Meningococcal vaccine development: a novel approach, Exp. Opin. Invest. Drugs 7(2):245-252 (1998).
Costantino, P et al., Development and phase 1 clinical testing of a conjugate vaccine against meningococcus A and C, Vaccine 10(10):691-698 (1992).
Cadoz, M et al, Tetravalent (A, C, Y, W 135) meningococcal vaccine in children: immunogenicity and safety, Vaccine 3:340-342 (1985).
Beuvery, EC et al., Immunological Evaluation of Meningococcal Group C Polysaccharide-Tetanus Toxoid Conjugate in Mice, Infect. Immun. 41(2):609-617 (1983).
Andre, FE et al., Conventional and New Generation Combined Vaccines, in Modern Vaccinology, Ed. E. Kurstak, Plenum Publishing Corp., Chap. 3, pp. 41-54 (1994).
Ambrosch, F et al., Immunogenicity and side-effects of a new tetravalent meningococcal polysaccharide vaccine, Bulletin of the World Health Organization, 61 (2): 317-323 (1983).
Twumasi, PA et al., A Trial of Group A plus Group C Meningococcal Polysaccharide-Protein Conjugate Vaccine in African Infants, J. Infect. Dis. 171:632-638 (1995).
Tai, JY et al., Preclinical evaluation of a combination vaccine against groups A, B, and C meningococci in both mice and nonhuman primates, Conjugate and Polysaccharide Vaccines (IPNC 1996).
Anderson, EL et al., Safety and Immunogenicity of Meningococcal A and C Polysaccharide Conjugate Vaccine in Adults, Infect. Immun. 62(8):3391-3395 (1994).
Costantino, P. et al., Size fractionation of bacterial capsular polysaccharides for their use in conjugate vaccines, Vaccine 17:1251-1263 (1999).
Fairley, CK et al., Conjugate Meningococcal Serogroup A and C Vaccine: Reactogenicity and Immunogenicity in United Kingdom Infants, J. Infect. Dis. 174:1360-1363 (1996).
Jones, DH, Menjugate Chiron, Current Opinion in Investigational Drugs 2(1):47-49 (2001).
MacLennan, J. et al., Immunologic Memory 5 Years after Meningococcal A/C Conjugate Vaccination in Infancy, J. Infect. Dis. 183:97-104 (2001).
Porro, M et al., Immunoelectrophoretic characterization of the molecular weight polydispersion of polysaccharides in multivalent bacterial capsular polysaccharide vaccines, J. Biological Standard. 11:65-74 (1983).
Ravenscroft, N et al., Physiochemical Characterisation of the Oligosaccharide Component of Vaccines, in Physio-Chemical Procedures for the Charactersation of Vaccines (Les Pensieres, Veyrier-du-Lac, France, Dec. 1-3, 1999) Krager, pp. 35-47 (2000).
Ravenscroft, N et al., Size determination of bacterial capsular oligosaccharides used to prepare conjugate vaccines, Vaccine 17:2802-2816 (1999).
Porro, M et al., A Molecular Model of Artificial Glycoprotein With Predetermined Multiple Immunodeterminants for Gram-Positive and Gram-Negative Encapsulated Bacteria, Mol. Immunol. 23(4):385-391 (1986).
Schutze, M-P et al., Carrier Induced Epitopic Suppression, A Major Issue for Future Synthetic Vaccines, J. Immunol. 135(4):2319-2322 (1985).
Schuchat, A et al., Bacterial Meningitis in the United States 1n 1995, N. Engl. J. Med. 337:970-976 (1997).
Renjifo, X et al., Carrier-Induced, Hapten-Specific Suppression: A Problem of Antigen Presentation, J. Immunol. 161:702-706 (1998).
Kaplan, SL et al., Multicenter Surveillance of Invasive Meningococcal Infections in Children, Pediatrics 118:e979-e984 (2006).
Global Alliance for Vaccines and Immunization, Fourth Board Meeting, Noordwijk, Netherlands (Nov. 19, 2000), pp. 1-7, 42-44, 53.
Goebel, WF, Chemo-Immunological Studies on Conjugated Carbohydrate-Proteins, J. Exp. Med. 68(4):469-484 (1938).
Gotschlich, EC et al., Human Immunity to Meningococcus, J. Exp. Med. 129(6):1349-1365 (1969).
Robbins, JB, Vaccines for the Prevention of Encapsulated Bacterial Diseases: Current Status, Problems and Prospects for the Future, Immunochemistry 15:839-854 (1978).
Jennings, HJ et al., Structures of the Capsular Polysaccharides of Neisseria meningitidis as Determiner by 13Carbon Nuclear Magnetic Resonance Spectroscopy, J. Infect. Dis. 136 (Suppl): S78-S83 (1977).
Bundle, DR et al., Determination of the Structure and Conformation of Bacterial Polysaccharides by Carbon 13 Nuclear Magnetic Resonance, J. Biol. Chem. 249(7):2275-2281 (1974).
Campagne, G et al., Development of a Meningococcal A/C Conjugate Vaccine, American Society of Tropical Medicine and Hygine, 46th Annual Meeting, Dec. 7-11, 1997, Disney's Coronado Springs Resort, Lake Buena Vista, FL, Abstract 81.
Lindberg, AA, Polyosides (encapsulated bacteria), C.R. Acad. Sci. III 322(11):925-932 (1999).
Lamb, DH et al., Capillary Electrophoretic Analysis of Meningococcal Polysaccharide—Diphtheria Conjugate Vaccines, in Physio-Chemical Procedures for the Characterization of Vaccines, Brown F. et al. (eds.), Dev. Biol. Basel Karger, 103:251-258 (2000).
Lei, QP et al., Quantification of Free Polysaccharide in Meningococcal Polysaccharide-Diphtheria Toxoid Conjugate Vaccines, in Physio-Chemical Procedures for the Characterization of Vaccines, Brown F. et al. (eds.), Dev. Biol. Basel Karger, 103:259-264 (2000).
Campagne, G et al., Safety and immunogenicity of three doses of a Neisseria A+C diphtheria conjugate vaccine in infants from Niger, Pediatr. Infect. Dis. 19:144-150 (2000).
Fusco, PC et al., Preclinical Studies on a Group Y Meningococcal Conjugate Vaccine, Intersci. Conf. Antimicrob. Agents Chemother., Sep. 23-26, 1999, 39:362, Abstract 251.
Leach et al. Induction of Immunologic Memory in Gambian Children by Vaccination in Infancy with a Group A plus Group C Meningococcal Polysaccharide-Protein Conjugate Vaccine, JID, vol. 175, No. 1, 1997, pp. 200-204.
Borrow et al. Immunogenicity of, and Immunologic Memory to, a Reduced Primary Schedule of Meningococcal C-Tetanus Toxoid Conjugate Vaccine in Infants in the United Kingdom. Infect. Immun., vol. 71, No. 10, 2003, pages 5549-5555.
Immunization Schedule in the USA. Located at http://www.drpaul. com/immunizations/immun-us.html, visited on May 16, 2011.
U.S. Heath National Institutes of Health, "Immunogenicity and Safety of Men ACWY in Infants (6 & 12 Months)", Apr. 4, 2006, pp. 1, Clinic trials.gov Archive, Washington, D.C., USA.
Centers for Disease Control and Prevention, "Licensure of a Meningococcal Conjugate Vaccine (MENVEO) and Guidance for Use—Advisory Committee on Immunization Practices (ACIP), 2010," Mar. 12, 2010, pp. 1-2, Morbidity and Mortality Weekly Report, Centers for Disease Control and Prevention, Atlanta, GA, USA.

(56) References Cited

OTHER PUBLICATIONS

Department of Health and Human Services FDA/CBER/OVRR/ DBPAP, "Memorandum-Novartis Vaccines and Diagnostics, Inc. Meningococcal (Groups A, C, Y and W-135) Oligosaccharide Diphtheria CRM197 Conjugate Vaccine," Jan. 28, 2010, pp. 1-80, Department of Health & Human Services, FDA, Washington, D.C.-USA.

MacLennan, J., "Meningococcal group C conjugate vaccines," Arch, Dis. Child, No. 84, May 2001, pp. 383-386, BMJ Publishing Group, LTD, London UK.

Siber, George R., "Pneumococcal Disease: Prospects for a New Generation of Vaccines," Science, vol. 265, Sep. 2, 1994, pp. 1385-1387, American Association for the Advancement of Science, Washington, D.C.-USA.

Halperin, S., et al., "Simultaneous administration of meningococcal C conjugate vaccine and diphtheria-tetanus-acellelar pertussis-inactivated poliovirus-Haemophilus influenzae type b conjugate vaccine in children: a randomized double-blind study," Clin. Invest. Med., vol. 25, No. 6, Dec. 2002, pp. 243-251, Canadian Medical Association, Ottawa, Canada.

Plotkin, S., et al., "Vaccines, 4th Edition, Chapter 34" Saunders, Elsevier, Inc., 2004, pp. 959-987.

Sanofi Pastuer, "284 Menactra®-Highlights of Prescribing Information," Nov. 30, 2011.

Rennels, M., et al., "Dose Escalation, Safety and Immunogencity Study of a Tetravalent Meningococcal Polysaccharide Diphtheria Conjugate Vaccine in Toddlers," Ped. Inf. Dis. J., vol. 21, No. 10, Oct. 2002, pp. 978-979, Lippincott Williams & Wilkins, Philadelphia, PA, USA.

World Health Organization, "Requirements for Meningococcal Polysaccharide vaccine, Annex 2," Tech. Rep. Ser. 594, 1975, pp. 50-75.

Trotter, C., et al., "Effectiveness of meningococcal serogroup C conjugate vaccine 4 years after introduction," The Lancet, vol. 364, Issue 9431, Jul. 2004, pp. 365-367, Reed Elsevier, GB LTD, UK.

Centers for Disease Control and Prevention, "Recommended Childhood and Adolescent Immunization Schedule—United States 2006," Jan. 6, 2006, pp. 1-4, Morbidity and Mortality Weekly Report, vol. 54, Nos. 51&52, Centers for Disease Control and Prevention, Atlanta, GA, USA.

Opponent's (GSK) Opposition Statement against the grant of European Patent Application No. 07753720.7; filed Jan. 24, 2013.

GSK's Notice of Opposition against the grant of European Patent Application No. 07753720.7; dated Jan. 24, 2013.

Opponent's (Pfizer) Opposition Statement against the grant of European Patent Application No. 07753720.7; filed Jan. 25, 2013.

Pfizer's Notice of Opposition against the grant of European Patent Application No. 07753720.7; filed Jan. 25, 2013.

Patentee's Reply to Notice of Opposition in European Patent Application No. 07753720.7; filed Sep. 13, 2013.

Rosenstein, N.E. et al., "The Changing Epidemiology of Meningococcal Disease in the United States, 1992-1996", J. Infect. Dis. 180(6):1894-1901 (1999).

Halperin, S.A. et al., "Safety and immunogenicity of an investigational quadrivalent meningococcal conjugate vaccine after one or two doses given to infants and toddlers", Eur. J. Clin. Microbiol. Infect. Dis. 29(3):259-267 (2010).

Perrett, K.P. et al., "Immunogenicity and Immune Memory of a Nonadjuvanted Quadrivalent Meningococcal Glycoconjugate Vaccine in Infants", Pediatri. Infect. Dis. J. 28(3):186-193 (2009).

Klein, N.P. et al., "Safety and Immunogenicity of a Novel Quadrivalent Meningococcal CRM-conjugate Vaccine Given Concomitantly With Routine Vaccinations in Infants", Pediatri. Infect. Dis. J. 31(1):64-71 (2012).

Klein, N.P. et al., "One or Two Doses of Quadrivalent Meningococcal Serogroups A, C, W-135 and Y Tetanus Toxoid Conjugate Vaccine Is Immunogenic in 9- to 12-Month-Old Children", Pediatri. Infect. Dis. J. 32(7): 760-767 (2013).

Pina, L.M. et al., "Safety and Immunogenicity of a Quadrivalent Meningococcal Polysaccharide Diphtheria Toxoid Conjugate Vaccine in Infants and Toddlers: Three Multicenter Phase III Studies", Pediatri. Infect. Dis. J. 31 (11):1173-1183 (2012).

Snape, M.D. et al., "Immunogenicity of a TetravalentMeningococcal Glycoconjugate Vaccine in Infants", JAMA 299 (2):173-184 (2008).

Novartis Vaccines and Diagnostics, "Menveo - Highlights of Prescribing Information" as revised Aug. 2013, pp. 1-27.

Glaxosmithkline. "NIMENRIX Package leaflet: Information for the user", pp. 1-47 No publication date.

Danzig, Lisa. (2004). "Meningococcal Vaccines," Ped. Infect. Dis. J., 23(12):5285-5292.

Granoff et al. (2005). "Persistence of group C anticapsular antibodies two to three years after immunization with an investigational quadrivalent Neisseria meningitidis-diphtheria toxoid conjugate vaccine," Ped. Infect. Dis. J., 24(2):132-136.

Granoff et al. (2004). "Protective activity of group C anticapsular antibodies elicited in two-year-olds by an investigational quadrivalent Neisseria meningitidis-diphtheria toxoid conjugate vaccine," Ped. Infect. Dis. J. 23(6):490-497.

Pichichero et al. (2005). "Comparative trial of the safety and immunogenicity of quadrivalent (A, C, Y, W-135) meningococcal polysaccharide-diphtheria conjugate vaccine versus quadrivalent polysaccharide vaccine in two- to ten-year-old children," Ped. Infect. Dis. J. 24(1):57-62.

Chippaux et al. (2004). "Immunogenicity, safety, and memory of different schedules of Neisseria meningitidis A/C-diphtheria toxoid conjugate vaccine in infants in Niger," Vaccine 22:3303-3311.

Product Information for Menomune A/C/Y/W-135, 2005, 6 pages.

U.S. Appl. No. 60/713,801,"Vaccines," filed Sep. 1, 2005, 41 pages.

Rappuoli et al., Glycoconjugate vaccines: Principles and mechanisms, Science Translational Medicine, Aug. 29, 2018, vol. 10, Issue 456, DOI: 10.1126/scitranslmed.aat4615.

* cited by examiner

REGIMENS FOR IMMUNISATION WITH MENINGOCOCCAL CONJUGATES

RELATED APPLICATIONS

This application claims the benefit of U.S. Provisional Application No. 60/997,781 filed Oct. 4, 2007 and is a continuation-in-part of U.S. Pat. No. 10,543,265, which issued from U.S. application Ser. No. 12/225,501, which is the U.S. National Phase of International Application No. PCT/US2007/007115, filed Mar. 22, 2007 and published in English, which claims the benefit of U.S. Provisional Application No. 60/785,234, filed Mar. 22, 2006. This application is also related to U.S. application Ser. No. 11/726,656, filed Mar. 22, 2007. The teachings of the above applications are incorporated in their entirety by reference.

TECHNICAL FIELD

This invention is in the field of immunising patients with meningococcal conjugates.

BACKGROUND OF THE INVENTION

Conjugate vaccines for *N. meningitidis* serogroup C have been approved for human use, and include the products known as Menjugate™, Meningitec™ and NeisVac-C™. Bivalent mixtures of conjugates from serogroups A+C [1,2] and C+Y [3] have also been reported. Mixtures of conjugates from all four of serogroups A, C, W135 and Y are also known (e.g. see references 4-8), including the Menactra™ product that was licensed in 2005.

In addition to the antigens included in a vaccine, an important aspect of effective immunisation is the dosing schedule. As noted in chapter 8 of reference 9, "most vaccines require administration of multiple doses in a primary series for development of immunity". Moreover, "periodic revaccination ('booster doses') with certain vaccines may be necessary to maintain immunity".

Known schedules for serogroup C meningococcal conjugate vaccines include: a single dose at 12 months of age; two doses at 2 & 4 months; three doses at 2, 3 & 4 months of age; three doses at 2, 4 & 6 months of age; three doses at 3, 5 & 12 months of age; three doses at 2, 4 & 12 months. Alternative schedules, including the potential for a dose in late infancy or the second year of life, have been suggested [10].

Multivalent meningococcal conjugate combinations have been administered according to various dosing schedules. For example, known single-dose schedules for multivalent meningococcal conjugate vaccines include: at 14 weeks of age [11]; at 6 months of age [12]; at 9 months [11]; between 12-16 months [13]; between 2-3 years of age [4,14]; between 2-10 years [15,16,17]; between 11-18 years [17]; 18-50 years [18]; 18-55 years [17]. The prescribing information for Menactra™ shows that it is administered as a single dose in 11-18 or 18-55 year olds.

Known 2-dose schedules for multivalent meningococcal conjugate vaccines include: 2 & 6 months of age [12]; first dose at 14 weeks of age, second dose at 9 months of age [11]; first dose at 12-15 months, second dose 2 months later [4]; first dose at 12-16 months, second dose 1 month later [13]; doses in 2 year olds at time zero and then 2 months later [17]; in adults at time zero and then 6 weeks later [1]; in adults at time zero and then 2 months later [2]. A clinical study has also been reported in which patients received a first dose aged 11-18 years and a second dose 3 years later.

Known 3-dose schedules for multivalent meningococcal conjugate vaccines include: 6, 10 and 14 weeks of age [4,11]; 2, 3 & 4 months [12]; 2, 4 & 6 months of age [17]; 3, 4 & 5 months of age [19].

A 4-dose schedule at 6 weeks, 10 weeks, 14 weeks and 9 months is disclosed in reference 11.

It is an object of the invention to provide further and improved schedules for administering multivalent meningococcal conjugate vaccines, in particular to children.

SUMMARY OF THE INVENTION

The present invention relates to methods for immunizing a patient, comprising: (a) administering a multivalent meningococcal conjugate vaccine to the patient when the patient is aged between 0 and 12 months; and (b) administering a multivalent meningococcal conjugate vaccine to the patient when the patient is aged between 12 and 24 months. The present invention also relates to methods for immunizing a patient who previously received a multivalent meningococcal conjugate vaccine when the patient was aged between 0 and 12 months, comprising: administering a multivalent meningococcal conjugate vaccine to the patient when the patient is aged between 12 and 24 months. In a particular embodiment, a multivalent meningococcal conjugate vaccine is administered to the patient at least twice while the patient is aged between 0 and 12 months and at least once while the patient is aged between 12 and 24 months.

The invention further relates to kits comprising: (a) a multivalent meningococcal conjugate vaccine; and (b) instructions for administering the vaccine according to a schedule that includes: (a) first administering the vaccine to a patient when the patient is aged between 0 and 12 months; and (b) then administering the vaccine to the patient when the patient is aged between 12 and 24 months.

The invention also relates to uses of a plurality of meningococcal conjugates in the manufacture of a medicament for administering to a patient in an immunisation schedule comprising: (a) administering the medicament to the patient when the patient is aged between 0 and 12 months; and (b) administering the medicament to the patient when the patient is aged between 12 and 24 months. The invention further relates to uses of a plurality of meningococcal conjugates in the manufacture of a medicament for administering to a patient who is aged between 12 and 24 months and who previously received a multivalent meningococcal conjugate vaccine when they were aged between 0 and 12 months.

In one embodiment, the multivalent meningococcal conjugate vaccine includes capsular saccharides from at least two of meningococcal serogroups A, C, W135 and Y. In a second embodiment, the multivalent meningococcal conjugate vaccine includes capsular saccharides from all four of meningococcal serogroups A, C, W135 and Y. In a preferred embodiment, the multivalent meningococcal conjugate vaccine includes a meningococcal serogroup Y conjugate.

In another embodiment, a dose in the 0-12 month period and a dose in the 12-24 month period are administered ≥6 months apart. In a further embodiment, a dose in the 0-12 month period is administered at 2 months, 3 months, 4 months, 5 months or 6 months of age. In another embodiment, a dose in the 12-24 month period is administered at between 12-15 months of age or at between 15-18 months of age.

In a further embodiment, a dose in the 0-12 month period is administered at substantially the same time as a hepatitis B virus vaccine, a diphtheria vaccine, a tetanus vaccine, a pertussis vaccine, a *Haemophilus influenzae* type b vaccine, a *Streptococcus pneumoniae* vaccine, and/or a polio vaccine. In another embodiment, a dose in the 12-24 month period is administered at substantially the same time as a hepatitis B virus vaccine, a diphtheria vaccine, a tetanus vaccine, a pertussis vaccine, a *Haemophilus influenzae* type b vaccine, a *Streptococcus pneumoniae* vaccine, a polio vaccine, an influenza vaccine, a chickenpox vaccine, a measles vaccine, a mumps vaccine, and/or a rubella vaccine.

In a particular embodiment, the multivalent meningococcal conjugate vaccine has a carrier protein selected from the group consisting of diphtheria toxoid, tetanus toxoid and CRM197. In another embodiment, the multivalent meningococcal conjugate vaccine is unadjuvanted.

DETAILED DESCRIPTION OF THE INVENTION

According to a first aspect of the invention, multivalent meningococcal conjugate vaccines are administered according to a schedule in which a first dose is administered to a patient aged between 0 and 12 months, and a second dose is administered to a patient aged between 12 and 24 months. This schedule offers early protection than the existing licensed schedule, reduces the cost of immunisation by avoiding the need for a third immunisation, and the second dose can act as a booster dose for providing long-lasting protection.

Thus the invention provides a method for immunising a patient, comprising: (a) administering a multivalent meningococcal conjugate vaccine to the patient when they are aged between 0 and 12 months; and (b) administering a multivalent meningococcal conjugate vaccine to the patient when they are aged between 12 and 24 months.

The invention also provides a method for immunising a patient who previously received a multivalent meningococcal conjugate vaccine to the patient when they were aged between 0 and 12 months, comprising: administering a multivalent meningococcal conjugate vaccine to the patient when they are aged between 12 and 24 months.

The invention also provides the use of a plurality of meningococcal conjugates in the manufacture of a medicament for administering to a patient in an immunisation schedule comprising: (a) administering the medicament to the patient when they are aged between 0 and 12 months; and (b) administering the medicament to the patient when they are aged between 12 and 24 months.

The invention also provides the use of a plurality of meningococcal conjugates in the manufacture of a medicament for administering to a patient who is aged between 12 and 24 months and who previously received a multivalent meningococcal conjugate vaccine when they were aged between 0 and 12 months.

The invention also provides a kit comprising: (a) a multivalent meningococcal conjugate vaccine; and (b) instructions for administering the vaccine according to a schedule that includes: (a) first administering the vaccine to a patient when they are aged between 0 and 12 months; and (b) then administering the vaccine to a patient when they are aged between 12 and 24 months.

According to a second aspect of the invention, multivalent meningococcal conjugate vaccines are administered according to a schedule in which at least two doses are administered to a patient aged between 0 and 12 months, and a further dose is administered to a patient aged between 12 and 24 months.

Thus the invention provides a method for immunising a patient, comprising: (a) administering a multivalent meningococcal conjugate vaccine to the patient at least twice while they are aged between 0 and 12 months; and (b) administering a multivalent meningococcal conjugate vaccine to the patient at least once while they are aged between 12 and 24 months.

The invention also provides a method for immunising a patient who previously received a multivalent meningococcal conjugate vaccine at least twice while they were aged between 0 and 12 months, comprising: administering a multivalent meningococcal conjugate vaccine to the patient while they are aged between 12 and 24 months.

The invention also provides the use of a plurality of meningococcal conjugates in the manufacture of a medicament for administering to a patient in an immunisation schedule comprising: (a) administering the medicament to the patient at least twice while they are aged between 0 and 12 months; and (b) administering the medicament to the patient at least once while they are aged between 12 and 24 months. The invention also provides the use of a plurality of meningococcal conjugates in the manufacture of a medicament for administering to a patient who is aged between 12 and 24 months and who previously received a multivalent meningococcal conjugate vaccine at least twice while they were aged between 0 and 12 months.

The invention also provides a kit comprising: (a) a multivalent meningococcal conjugate vaccine; and (b) instructions for administering the vaccine according to a schedule that includes: (a) first administering the vaccine to a patient at least twice while they are aged between 0 and 12 months; and (b) then administering the vaccine to a patient at least once when they are aged between 12 and 24 months.

The invention also provides a multivalent meningococcal conjugate vaccine for use in a method for immunising a patient that comprises: (a) administering a multivalent meningococcal conjugate vaccine to the patient at least twice while they are aged between 0 and 12 months; and (b) administering a multivalent meningococcal conjugate vaccine to the patient at least once while they are aged between 12 and 24 months. The invention also provides a multivalent meningococcal conjugate vaccine for use in a method for immunising a patient while they are aged between 12 and 24 months, wherein the patient previously received a multivalent meningococcal conjugate vaccine at least twice while they were aged between 0 and 12 months.

The invention may be used in particular to deliver meningococcal conjugates in a three-dose regimen with doses at 2 months, 4 months and 12 months. The invention may also be used in particular to deliver meningococcal conjugates in a four-dose regimen with doses at (i) 2 months, 3 months, 4 months and 12 months, or (ii) 2 months, 4 months, 6 months and 12 months.

The Schedule of the First Aspect

The schedule of the first aspect of the invention involves a first dose in the first year of life and a second dose in the second year of life. The first dose is given to a patient aged between 0 and 12 months, up to but not including their first birthday. The second dose is given to a patient aged 12 and 24 months, starting on the day of their first birthday, up to and including their second birthday.

Within this overall schedule, the two doses can be administered at any time. In general, however, the two doses will be administered at least 4 weeks apart e.g. ≥8 weeks apart, ≥2 months apart, ≥3 months apart, ≥6 months apart, etc.

Within the 0-12 month period, the first dose is preferably not administered before about 6 weeks of age, and is administered after at least 5 weeks of age. Typical times for receiving the first dose are at 2 months, 3 months, 4 months, 5 months or 6 months of age.

Within the 12-24 month period, the second dose is preferably administered in the first half i.e. between 12 and 18 months e.g. between 12 and 15 months of age, or between 15 and 18 months.

The patient will not have received a meningococcal conjugate vaccine before the first dose in the schedule. In preferred embodiments, the patient does not receive a meningococcal conjugate vaccine between the first dose and the second dose, but sometimes an intermediate dose may be administered. For example, the patient may receive 2 or 3 doses in the 0-12 month period e.g. at 2, 3 & 4 months of age, at 3, 4 & 5 months of age, at 2, 4 & 6 months, at 3, 5 & 9 months etc.

In some embodiments, the patient does not receive a further dose, but in other embodiments they can do so. Such a further dose is preferably not administered until after the patient's second birthday e.g. until after their fifth birthday, after their tenth birthday, after their fifteenth birthday, after their seventeenth birthday, after their twenty-first birthday, etc. The further dose may be administered when circulating antibody levels have declined to undetectable levels [20].

Conveniently, the first dose can be administered at substantially the same time as (e.g. during the same medical consultation or visit to a healthcare professional) another vaccine e.g. at substantially the same time as a hepatitis B virus vaccine, a diphtheria vaccine, a tetanus vaccine, a pertussis vaccine (either cellular or, preferably, acellular), a *Haemophilus influenzae* type b vaccine, a *Streptococcus pneumoniae* vaccine, and/or a polio vaccine (preferably in inactivated poliovirus vaccine). Each of these optionally co-administered vaccines may be a monovalent vaccine or may be part of a combination vaccine (e.g. as part of a D-T-P vaccine).

Conveniently, the second dose can be administered at substantially the same time as (e.g. during the same medical consultation or visit to a healthcare professional) another vaccine e.g. at substantially the same time as a hepatitis B virus vaccine, a diphtheria vaccine, a tetanus vaccine, a pertussis vaccine (either cellular or acellular), a *Haemophilus influenzae* type b vaccine, a *Streptococcus pneumoniae* vaccine, a polio vaccine (preferably in inactivated poliovirus vaccine), an influenza vaccine, a chickenpox vaccine, a measles vaccine, a mumps vaccine, and/or a rubella vaccine. Each of these optionally co-administered vaccines may be a monovalent vaccine or may be part of a combination vaccine (e.g. as part of a M-M-R vaccine).

The Schedule of the Second Aspect

The schedule of the second aspect of the invention involves two doses in the first year of life and a further dose in the second year of life. The first two doses are given to a patient aged between 0 and 12 months, up to but not including their first birthday. The further dose is given to a patient aged 12 and 24 months, starting on the day of their first birthday, up to and including their second birthday.

Within this overall schedule, the doses can be administered at any time. In general, however, each of the doses will be administered at least 4 weeks apart e.g. ≥8 weeks apart, ≥2 months apart, ≥3 months apart, ≥4 months apart, etc.

Within the 0-12 month period, the first dose is preferably not administered before about 6 weeks of age e.g. it is administered after 5 weeks. Typical times for receiving the first dose are at 2 months, 3 months, 4 months, 5 months or 6 months of age. The second dose will typically be administered at least 1 month after the first dose e.g. at 3 months, 4 months, 5 months, 6 months or 7 months of age. An interval of 1, 2 or 3 months between the first two doses is usual e.g. a dose at 2 and 4 months.

Within the 12-24 month period, the at least one dose is preferably administered in the first half i.e. between 12 and 18 months e.g. between 12 and 15 months of age, or between 15 and 18 months. A dose in month 12, 13 or 14 is convenient.

The patient will not have received a meningococcal conjugate vaccine before the first dose in the schedule. After the second dose, the patient usually does not receive a meningococcal conjugate vaccine before receiving the at least one dose in the 12-24 month period, but sometimes an intermediate dose may be administered. For example, the patient may receive three doses in the 0-12 month period e.g. at 2, 3 & 4 months of age, at 3, 4 & 5 months of age, at 2, 4 & 6 months, at 3, 5 & 9 months etc.

In some embodiments, the patient receives only a single dose in the 12-24 month period, but in other embodiments they may receive additional doses e.g. two or three doses.

Overall, though, administration of only three doses in the 0-24 month time period is usual with the second aspect of the invention.

A patient may receive additional dose(s) after their second birthday. Such a dose may be in the 24-36 month period but may be administered later than that e.g. after their fifth birthday, after their tenth birthday, after their twelfth birthday, after their fourteenth birthday, after their fifteenth birthday, after their seventeenth birthday, after their twenty-first birthday, etc. Such further dose(s) may be administered when circulating antibody levels have declined to undetectable levels [21].

Conveniently, the meningococcal conjugate vaccines given in the 0-12 month period can be administered at substantially the same time as (e.g. during the same medical consultation or visit to a healthcare professional) another vaccine e.g. at substantially the same time as a hepatitis B virus vaccine, a diphtheria vaccine, a tetanus vaccine, a pertussis vaccine (either cellular or, preferably, acellular), a *Haemophilus influenzae* type b vaccine, a *Streptococcus pneumoniae* vaccine, and/or a polio vaccine (preferably in inactivated poliovirus vaccine). Each of these optionally co-administered vaccines may be a monovalent vaccine or may be part of a combination vaccine (e.g. as part of a D-T-P vaccine or a higher-valency combination). Administration at the same time as a D-T-Pa, a D-T-Pa-Hib, a D-T-Pa-Hib-IPV or a D-T-Pa-Hib-HBsAg-IPV vaccine is useful. Administration at the same time as a pneumococcal conjugate vaccine is also useful. Thus a patient may receive three separate doses in a single occasion: meningococcal conjugate; pneumococcal conjugate; and a D-T-P-based combination vaccine.

Conveniently, the meningococcal conjugate vaccine(s) given in the 12-24 month period can be administered at substantially the same time as (e.g. during the same medical consultation or visit to a healthcare professional) another vaccine e.g. at substantially the same time as a hepatitis B virus vaccine, a diphtheria vaccine, a tetanus vaccine, a pertussis vaccine (either cellular or acellular), a *Haemophilus influenzae* type b vaccine, a *Streptococcus pneumoniae* vaccine (usually a mixture of conjugated capsular saccharides), a polio vaccine (preferably in inactivated poliovirus vaccine), an influenza vaccine, a chickenpox vaccine, a measles vaccine, a mumps vaccine, and/or a rubella vaccine. Each of these optionally co-administered vaccines may be a monovalent vaccine or may be part of a combination vaccine (e.g. as part of a M-M-R or M-M-R-V vaccine). Administration at the same time as a pneumococcal conjugate vaccine is particularly useful.

In some embodiments the patient will receive a vaccine between the two doses in the 0-12 month time period, but this vaccine will not include a meningococcal conjugate. For instance, a patient may receive meningococcal conjugates at 2 months and 4 months (e.g. at the same time as a DTP-based vaccine), with an intervening non-meningococcal dose at 3 months (e.g. just a DTP-based vaccine).

The Vaccine

The invention involves the administration of multivalent meningococcal conjugate vaccines i.e. vaccines that, when administered, simultaneously provide immunity against 2, 3, 4 or more different serotypes of *N. meningitidis*. Multivalent vaccines against 2, 3, or 4 of serogroups A, C, W135 and Y are preferred e.g. A+C, C+Y, W135+Y, A+W135+Y, A+C+W135+Y, etc. Vaccines including at least serogroup C are preferred (e.g. A+C), as are vaccines including at least serogroup Y. Vaccines including saccharides from all four of serogroups A, C, W135 and Y are most preferred.

The vaccines include a meningococcal capsular saccharide conjugated to a carrier protein.

The capsular saccharide of serogroup A meningococcus is a homopolymer of (α1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are O-acetylated at the C-3 position. Acetyl groups can be replaced with blocking groups to prevent hydrolysis [22], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8OAc-(α2→. Most serogroup C strains have O-acetyl groups at C-7 and/or C-8 of the sialic acid residues, but about 15% of clinical isolates lack these O-acetyl groups [23,24]. The presence or absence of OAc groups generates unique epitopes, and the specificity of antibody binding to the saccharide may affect its bactericidal activity against O-acetylated (OAc+) and de-O-acetylated (OAc−) strains [25-27]. Serogroup C saccharides used with the invention may be prepared from either OAc+ or OAc-strains. Licensed Men-C conjugate vaccines include both OAc−(NEISVAC-C™) and OAc+ (MENJUGATE™ & MENINGITEC™) saccharides. In some embodiments, strains for production of serogroup C conjugates are OAc+ strains, e.g. of serotype 16, serosubtype P1.7a,1, etc. Thus C:16:P1.7a,1 OAc+ strains may be used. OAc+ strains in serosubtype P1.1 are also useful, such as the C11 strain.

The serogroup W135 saccharide is a polymer of sialic acid-galactose disaccharide units. Like the serogroup C saccharide, it has variable O-acetylation, but at sialic acid 7 and 9 positions [28]. The structure is written as: →4)-D-Neup5Ac(7/9OAc)-α-(2→6)-D-Gal-α-(1→.

The serogroup Y saccharide is similar to the serogroup W135 saccharide, except that the disaccharide repeating unit includes glucose instead of galactose. Like serogroup W135, it has variable O-acetylation at sialic acid 7 and 9 positions [28]. The serogroup Y structure is written as: →4)-D-Neup5Ac(7/9OAc)-α-(2→6)-D-Glc-α-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides.

The saccharide moieties in conjugates may comprise full-length saccharides as prepared from meningococci, and/or may comprise fragments of full-length saccharides i.e. the saccharides may be shorter than the native capsular saccharides seen in bacteria. The saccharides may thus be depolymerized, with depolymerisation occurring during or after saccharide purification but before conjugation. Depolymerisation reduces the chain length of the saccharides. One depolymerisation method involves the use of hydrogen peroxide [4]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [4]. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. In some embodiments, saccharides have the following range of average degrees of polymerisation (Dp): A=10-20; C=12-22; W135=15-25; Y=15-25. In terms of molecular weight, rather than Dp, useful ranges are, for all serogroups: <100 kDa; 5 kDa-75 kDa; 7 kDa-50 kDa; 8 kDa-35 kDa; 12 kDa-25 kDa; 15 kDa-22 kDa (saccharide MW).

In some embodiments, the average molecular weight for saccharides from each of meningococcal serogroups A, C, W135 and Y may be more than 50 kDa e.g. ≥75 kDa, ≥100 kDa, ≥110 kDa, ≥120 kDa, ≥130 kDa, etc. [29], and even up to 1500 kDa, in particular as determined by MALLS. For instance: a Men-A saccharide may be in the range 50-500 kDa e.g. 60-80 kDa; a Men-C saccharide may be in the range 100-210 kDa; a Men-W135 saccharide may be in the range 60-190 kDa e.g. 120-140 kDa; and/or a Men-Y saccharide may be in the range 60-190 kDa e.g. 150-160 kDa.

The mass of meningococcal saccharide per serogroup in the reconstituted vaccine will usually be between 1 µg and 20 µg e.g. between 2 and 10 µg per serogroup, or about 4 µg or about 5 µg or about 10 µg. Where conjugates from more than one serogroup are included then they may be present at substantially equal masses e.g. the mass of each serogroup's saccharide is within +10% of each other. As an alternative to an equal ratio, a double mass of serogroup A saccharide may be used. Thus a vaccine may include Men-A saccharide at 10 µg and Men-C, -W135 and -Y saccharides at 5 µg each.

Typical carrier proteins for use in conjugates are bacterial toxins, such as diphtheria toxin [e.g. see chapter 13 of ref. 9; refs. 30-33] (or its CRM197 mutant [34-37]) and tetanus toxin, usually in toxoid form (e.g. obtained by treatment with an inactivating chemical, such as formalin or formaldehyde). Other suitable carrier proteins include the *N. meningitidis* outer membrane protein complex [38], synthetic peptides [39,40], heat shock proteins [41,42], pertussis proteins [43,44], cytokines [45], lymphokines [45], hormones [45], growth factors [45], artificial proteins comprising multiple human $CD4^+$ T cell epitopes from various pathogen-derived antigens [46] such as N19 [47], protein D from *H. influenzae* [48-50], pneumolysin [51] or its non-toxic derivatives [52], pneumococcal surface protein PspA [53], iron-uptake proteins [54], toxin A or B from *C. difficile* [55], recombinant *Pseudomonas aeruginosa* exoprotein A (rEPA) [56], etc.

A single carrier protein may carry saccharides from multiple different serogroups [57], but this arrangement is not preferred. Conjugates are preferably prepared separately and then mixed. Thus it is preferred not to use a single protein carrying multiple serogroups (cf. references 57 & 58). After mixing, the concentration of the mixed conjugates can be adjusted e.g. with sterile pyrogen-free, phosphate-buffered saline. Where the lyophilized component includes conjugates from more than one meningococcal serogroup then the various conjugates may use different carrier proteins (e.g. one serogroup on CRM197, another on tetanus toxoid) or they may use the same carrier protein (e.g. saccharides from two serogroups separately conjugated to CRM197 and then combined).

Four particularly preferred carrier proteins are diphtheria toxoid (Dt), tetanus toxoid (Tt), CRM197 and protein D from *H. influenzae*. These proteins are preferred because they are the main carriers currently in use in pediatric vaccines e.g. the Hib conjugates from GSK use Tt as the carrier, the HibTITER™ product uses CRM197, the pneumococcal conjugates in Prevenar™ use CRM197, the Menactra™ product uses Dt, the Menjugate™ and Meningitec™ products use CRM197, and NeisVac-C™ uses Tt.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. As described in reference 59, different meningococcal serogroup conjugates in a mixture can have different saccharide:protein ratios e.g. one may have a ratio of between 1:2 & 1:5, whereas another has a ratio between 5:1 & 1:1.99. Conjugates with saccharide: protein ratio of about 1:12 or about 1:3 are useful where the carrier is Dt. In some embodiments, a conjugate ideally has a weight excess of carrier protein.

The carrier molecule may be covalently conjugated to the meningococcal saccharide directly or via a linker. Various linkers are known e.g. an adipic acid linker, which may be formed by coupling a free —$NH_2$ group (e.g. introduced to a saccharide by amination) with adipic acid (using, for example, diimide activation), and then coupling a protein to the resulting saccharide-adipic acid intermediate [60,61]. Another preferred type of linkage is a carbonyl linker, which may be formed by reaction of a free hydroxyl group of a modified glucan with CDI [62,63] followed by reaction with a protein to form a carbamate linkage. Other linkers include β-propionamido [64], nitrophenyl-ethylamine [65], haloacyl halides [66], glycosidic linkages [67], 6-aminocaproic acid [68], N-succinimidyl-3-(2-pyridyldithio)-propionate (SPDP) [69], adipic acid dihydrazide ADH [70], $C_4$ to $C_{12}$ moieties [71], etc. Carbodiimide condensation can also be used [72].

Direct linkages to the protein may comprise oxidation of the polysaccharide followed by reductive amination with the protein, as described in, for example, references 73 and 74.

As described in reference 75, a mixture can include one conjugate with direct saccharide/protein linkage and another conjugate with linkage via a linker. This arrangement applies particularly when using saccharide conjugates from different meningococcal serogroups e.g. Men-A and Men-C saccharides may be conjugated via a linker, whereas Men-W135 and Men-Y saccharides may be conjugated directly to a carrier protein.

The saccharide will typically be activated or functionalized prior to conjugation. Activation may involve, for example, cyanylating reagents [76, 77, etc.]). Other suitable techniques use active esters, carbodiimides, hydrazides, norborane, p-nitrobenzoic acid, N-hydroxysuccinimide, S—NHS, EDC, TSTU; see also the introduction to reference 78).

A useful conjugation process involves: introduction of amino groups into the saccharide (e.g. by replacing terminal =O groups with —$NH_2$) followed by derivatisation with an adipic diester (e.g. adipic acid N-hydroxysuccinimide diester) and reaction with carrier protein (e.g. CRM197). Further details of this conjugation method can be found in reference 5. Conjugates obtainable by this method are preferred conjugates for use according to the invention.

In another useful conjugation process, a saccharide is reacted with adipic acid dihydrazide. For serogroup A, carbodiimide (EDAC) may also be added at this stage. After a reaction period, sodium cyanoborohydride is added. Derivatized saccharide can then be prepared e.g. by ultrafiltration. The derivatized saccharide is then mixed with carrier protein (e.g. with a diphtheria toxoid), and carbodiimide is added. After a reaction period, the conjugate can be recovered. Further details of this conjugation method can be found in reference 5. Conjugates obtainable by this method are preferred conjugates for use according to the invention e.g. conjugates comprising a diphtheria toxoid carrier and an adipic acid linker.

In another useful conjugation process, a saccharide is derivatized with a cyanylating reagent [77], followed by coupling to a protein (direct, or after introduction of a thiol or hydrazide nucleophile group into the carrier), without the need to use a linker. Suitable cyanylating reagents include 1-cyano-4-(dimethylamino)-pyridinium tetrafluoroborate ('CDAP'), p-nitrophenylcyanate and N-cyanotriethylammonium tetrafluoroborate ('CTEA'). CDAP is preferred, particularly where *H. influenzae* protein D is the common carrier. Direct coupling is preferred.

Administration of a conjugate preferably results in an increase in serum bactericidal assay (SBA) titre for the relevant serogroup of at least 4-fold, and preferably at least 8-fold, measured with human complement [79]. If rabbit complement is used to measure SBA titres then the titre increase is preferably at least 128-fold.

In compositions of the invention, the amount of carrier (conjugated and unconjugated) from each conjugate is preferably no more than 100 µg/ml e.g. <30 µg/ml of carrier protein from each conjugate. Preferred compositions include a total concentration of carrier (either solely for the combined meningococcal conjugates, or preferably for the composition as a whole) of less than 500 µg/ml e.g. <400 µg/ml, <300 µg/ml, <200 µg/ml, <100 µg/ml, <50 µg/ml, etc.

Vaccines of the invention may include no antigens other than the meningococcal conjugates. In some embodiments, however, vaccines may include further antigens. Thus they may include further antigens from other pathogens, particularly from bacteria and/or viruses. They may include other conjugated saccharides from non-meningococcal organisms and/or they may include non-saccharide antigens. For example, they may include one or more of the following:

a diphtheria toxoid ('D').
a tetanus toxoid ('T').
a pertussis antigen ('P'), which is typically acellular ('aP').
a hepatitis B virus (HBV) surface antigen ('HBsAg').
a hepatitis A virus (HAV) antigen.

a conjugated *Haemophilus influenzae* type b capsular saccharide ('Hib').

a conjugated *Streptococcus pneumoniae* capsular saccharide.

a protein from serogroup B of *N. meningitidis*.

a vesicle preparation from serogroup B of *N. meningitidis*.

inactivated poliovirus vaccine (IPV).

The schedule of the invention may use different vaccines for the first and second (first aspect) or the three (second aspect) specified doses e.g. the first vaccine may include non-meningococcal antigens whereas the second vaccine does not, or the first vaccine may include a first set of non-meningococcal antigens (e.g. DTP) whereas the second vaccine includes a second (different) set of non-meningococcal antigens (e.g. MMR), etc.

Where a composition includes a Hib conjugate then, in some embodiments, its mass will be substantially the same as the mean mass of meningococcal saccharide per serogroup. In some embodiments, the mass of Hib saccharide will be more than (e.g. at least 1.5×) the mean mass of meningococcal saccharide per serogroup. In some embodiments, the mass of Hib saccharide will be less than (e.g. at least 1.5×) the mean mass of meningococcal saccharide per serogroup [80].

In addition to the antigenic components described above, compositions of the invention will generally include a non-antigenic component. The non-antigenic component can include carriers, adjuvants, excipients, buffers, etc., as described in more detail below. These non-antigenic components may have various sources. For example, they may be present in one of the antigen or adjuvant materials that is used during manufacture or may be added separately from those components. Preferred compositions of the invention include one or more pharmaceutical carrier(s) and/or excipient(s). A thorough discussion of pharmaceutically acceptable carriers and excipients is available in reference 81.

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [82], but keeping osmolality in this range is nevertheless preferred.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition of the invention will generally be between 5.0 and 7.5, and more typically between 5.0 and 6.0 for optimum stability, or between 6.0 and 7.0.

Compositions of the invention are preferably sterile.

Compositions of the invention are preferably non-pyrogenic e.g. containing <1 EU (endotoxin unit, a standard measure) per dose, and preferably <0.1 EU per dose.

Compositions of the invention are preferably gluten free.

Where antigens are adsorbed, a composition may be a suspension with a cloudy appearance. This appearance means that microbial contamination is not readily visible, and so the vaccine preferably contains a preservative. This is particularly important when the vaccine is packaged in multidose containers. Preferred preservatives for inclusion are 2-phenoxyethanol and thimerosal. It is recommended, however, not to use mercurial preservatives (e.g. thimerosal) where possible. It is preferred that compositions of the invention contain less than about 25 ng/ml mercury.

The concentration of any aluminium salts in a composition of the invention, expressed in terms of $Al^{3+}$, is preferably less than 5 mg/ml e.g. ≤4 mg/ml, ≤3 mg/ml, ≤2 mg/ml, ≤1 mg/ml, etc.

Compositions of the invention are preferably administered to patients in 0.5 ml doses. References to 0.5 ml doses will be understood to include normal variance e.g. 0.5 ml±0.05 ml.

Residual material from individual antigenic components may also be present in trace amounts in the final vaccine produced by the process of the invention. For example, if formaldehyde is used to prepare the toxoids of diphtheria, tetanus and pertussis then the final vaccine product may retain trace amounts of formaldehyde (e.g. less than 10 μg/ml, preferably <5 μg/ml). Media or stabilizers may have been used during poliovirus preparation (e.g. Medium 199), and these may carry through to the final vaccine. Similarly, free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at ≤100 μg/ml, preferably <10 μg/ml, each. Other components from antigen preparations, such as neomycin (e.g. neomycin sulfate, particularly from an IPV component), polymyxin B (e.g. polymyxin B sulfate, particularly from an IPV component), etc. may also be present e.g. at sub-nanogram amounts per dose.

A further possible component of the final vaccine which originates in the antigen preparations arises from less-than-total purification of antigens. Small amounts of *B. pertussis, C. diphtheriae, C. tetani* and/or *S. cerevisiae* proteins and/or genomic DNA may therefore be present.

Meningococcal conjugates may be lyophilized prior to use according to the invention. If lyophilized, the composition may include a stabiliser such as mannitol. It may also include sodium chloride. A vaccine useful with the invention may be distributed in kit form with at least one lyophilized meningococcal conjugate and at least one aqueous meningococcal conjugate, with the aqueous material being used to reconstitute the lyophilized material prior to use. For example, a lyophilized MenA conjugate may be distributed with an aqueous mixture of MenC, MenW and MenY conjugates.

In some embodiments of the invention, the Menactra™ product may be used. In some embodiments of the invention, the vaccine described in reference 83 may be used.

The Human Patient

The age of patients receiving vaccines of the invention is dictated by the schedule.

Although the patient will not have received a meningococcal conjugate vaccine before the first dose in the schedule, they may have received other non-meningococcal conjugates and/or they may have received the carrier protein that is used in the meningococcal conjugate. Prior exposure to the carrier may have been as carrier in non-meningococcal conjugate (e.g. in a Hib conjugate) and/or as antigen itself (e.g. diphtheria toxoid may be used as the carrier for the meningococcal conjugates, but is also used as an antigen for protecting against *C. diphtheriae*; tetanus toxoid may be used as the carrier for the meningococcal conjugates, but is also used as an antigen for protecting against *C. tetani*).

After receiving the first dose in the schedule, and before the second dose, a patient is distinguishable from a person in the general population, as they will have mounted an immune response against the first dose. Thus patients waiting to receive the schedule's second dose (and, where applicable, later doses) are a specific and identifiable subset of the population. The patient may possess memory B cells against the pathogen. These memory cells may be activated by later doses such that they can rapidly proliferate and differentiate into plasma cells that secrete high-affinity serum antibodies.

Compositions of the invention can be administered by intramuscular injection e.g. into the arm, leg or buttock. Where another vaccine is co-administered then it is typical to inject compositions into opposite limbs e.g. to inject one into the left arm and one into the right arm.

Where compositions of the invention include an aluminium-based adjuvant, settling of components may occur during storage. The composition should therefore be shaken prior to administration to a patient. The shaken composition will generally be a turbid white suspension.

Packaging

Vaccines for use with the invention can be placed into containers for use. Suitable containers include vials and disposable syringes (preferably sterile ones).

Where a composition of the invention is packaged into vials, these are preferably made of a glass or plastic material. The vial is preferably sterilized before the composition is added to it. To avoid problems with latex-sensitive patients, vials are preferably sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe may or may not have a needle attached to it; in the latter case a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

If a vaccine is in lyophilized form then it will usually be resuspended into an aqueous form prior to administration. It may be reconstituted with an aqueous vaccine.

In addition to containing vaccines for administration, kits of the invention can include instructions for administering the vaccine. With the first aspect of the invention the instructions will refer to an immunisation schedule that includes: (a) first administering the vaccine to a patient when they are aged between 0 and 12 months; and (b) then administering the vaccine to a patient when they are aged between 12 and 24 months. With the second aspect of the invention the instructions will refer to an immunisation schedule that includes: (a) first administering the vaccine to a patient at least twice while they are aged between 0 and 12 months; and (b) then administering the vaccine to a patient at least once when they are aged between 12 and 24 months.

Adjuvants

Vaccines of the invention may include an adjuvant. Where a vaccine includes only meningococcal conjugates, however, use of an adjuvant is not preferred. Where an adjuvant is used, it may comprise one or more aluminium salts, and particularly an aluminium phosphate adjuvant and/or an aluminium hydroxide adjuvant.

Aluminium adjuvants currently in use are typically referred to either as "aluminium hydroxide" or as "aluminium phosphate" adjuvants. These are names of convenience, however, as neither is a precise description of the actual chemical compound which is present (e.g. see chapter 9 of reference 84). The invention can use any of the "hydroxide" or "phosphate" salts that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 84).

The adjuvants known as "aluminium phosphate" are typically aluminium hydroxyphosphates, often also containing a small amount of sulfate. They may be obtained by precipitation, and the reaction conditions and concentrations during precipitation can influence the degree of substitution of phosphate for hydroxyl in the salt. Hydroxyphosphates generally have a $PO_4/Al$ molar ratio between 0.3 and 0.99. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of ref. 84).

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate. Typical diameters of the particles are in the range 0.5-20 μm (e.g. about 5-10 μm) after any antigen adsorption.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

An aluminium phosphate solution used to prepare a composition of the invention may contain a buffer (e.g. a phosphate or a histidine or a Tris buffer), but this is not always necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

A mixture of both an aluminium hydroxide adjuvant and an aluminium phosphate adjuvant can be used. If so, there may be more aluminium phosphate than hydroxide e.g. a weight ratio of at least 2:1 e.g. ≥5:1, ≥6:1, ≥7:1, ≥8:1, ≥9:1, etc.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg is also preferred.

Amounts of conjugates are generally given in terms of mass of saccharide (i.e. the dose of the conjugate (carrier+ saccharide) as a whole is higher than the stated dose) in order to avoid variation due to choice of carrier.

Where animal (and particularly bovine) materials are used in the culture of cells, they should be obtained from sources that are free from transmissible spongiform encaphalopathies (TSEs), and in particular free from bovine spongiform encephalopathy (BSE).

EXAMPLES

Trial A

The immunogenicity, safety, tolerability and the ability to prime for memory of a meningococcal conjugate vaccine are investigated in a multi-centre, open-label, controlled, randomized study. Infants are split into three groups to receive an unadjuvated 4-valent conjugated A-C-W135-Y vaccine as follows, with the group 1 schedule being an embodiment of the invention:

1: first doses at about 6 months, then a second dose at about 12 months (on or after birthday)
2: single dose at about 12 months (on or after birthday)
3: dose of monovalent MenC at 12 months, then 4-valent at 18 months.

Meningococcal conjugates are administered at the same time as other routine pediatric vaccines, and blood samples for serological analysis are taken both at the time of vaccination and 1 month later:

|  | Visit 1 | Visit 2 | Visit 3 | Visit 4 |
|---|---|---|---|---|
| Group 1 | 6 months<br>B, M4, PC7, 5 | 7 months<br>B | 12 months<br>B, M4, PC7 | 13 months<br>B, 4V |
| Group 2 | 6 months<br>B, PC7, 5 | 7 months<br>B | 12 months<br>B, M4, PC7 | 13 months<br>B, 4V |
| Group 3 | 12 months<br>B, M1, PC7 | 13 months<br>B, 4V | 18 months<br>B, M4, 5 | 19 months<br>B |

Key: B = blood taken for serology; 5 = D-T-Pa-Hib-IPV; PC7 = 7-valent pneumococcal conjugate; 4V = MMR + V; M4 = 4-valent Men-A-C-W135-Y conjugates; M1 = Men-C conjugate.

Immunogenicity is assessed by evaluating serum antibody responses by measuring bactericidal antibody titers.

For blood samples taken at the first 2 visits, the bactericidal antibody titer at visit 2, expressed as a ratio relative to visit 1, was as follows for each group:

|  | A | C | W135 | Y |
|---|---|---|---|---|
| Group 1 | 1.5 | 11 | 2.8 | 1.8 |
| Group 2 | 1.0 | 1 | 1.0 | 1.0 |
| Group 3 | 1.0 | 20 | 1.0 | 1.0 |

Trial B

An open-label randomized study is used to investigate the serogroup A, C, W-135 and Y specific memory B cell response to a primary course of the tetravalent Men-ACWY vaccine disclosed in reference 5. The trial involves about 220 healthy infants in the UK. The Men-ACWY vaccine is administered to a subset of these infants at 2 months and 4 months as part of their existing 2,3,4-month course of D-T-Pa-Hib-IPV. It is co-administered at the same time as the first and third doses of this 5-valent vaccine, and at the same time as Prevnar™ pneumococcal conjugate vaccine.

In a booster phase, children in all groups receive a dose of the Men-ACWY vaccine at 12 months of age. Some patients receive Prevnar™ at the same time, whereas others receive Prevnar™ at 13 months instead. Patients may optionally receive a Hib conjugate (booster) and a MMR vaccine at a 13 month visit.

Thus patients receive one of the following two overall immunisation schedules:

| Visit (months)t | Group 1 | Group 2 |
|---|---|---|
| 2 | Men-ACWY<br>D-T-Pa-Hib-IPV/Prevnar | Men-ACWY<br>D-T-Pa-Hib-IPV/Prevnar |
| 3 | D-T-Pa-Hib-IPV | D-T-Pa-Hib-IPV |

-continued

| Visit (months)t | Group 1 | Group 2 |
|---|---|---|
| 4 | Men-ACWY D-T-Pa-Hib-IPV/Prevnar | Men-ACWY D-T-Pa-Hib-IPV/Prevnar |
| 12 | Men-ACWY | Men-ACWY Prevnar |
| 13 | Prevnar/(Hib)/(MMR) | (Hib)/(MMR) |

Blood samples are taken: (i) 30 days after the second dose i.e. at 5 months; (ii) at 12 months, immediately before the booster immunization; and (iii) at 13 months. In addition, all children will receive one additional blood draw at variable times. A blood sample is also taken from the mothers of all infants at the time of enrolment into the study. Blood samples are analysed by ELISA and SBA assays, and also by ELISpot and/or limiting dilution assay.

Trial C

In a different open-label randomized controlled trial (see reference 85, the full contents of which are incorporated herein by reference), the immunogenicity of the tetravalent Men-ACWY vaccine was tested in infants in the UK or Canada. The Men-ACWY vaccine was co-administered during the children's existing 2,3,4-month course of vaccinations, at the same time as either at (i) the first and third doses or (ii) each of the three doses. Thus half of the patients received Men-ACWY conjugates at 2 & 4 months and the other half patients received it at 2, 3 & 4 months. After this infant stage administration, patients then received a further dose of the Men-ACWY vaccine at 12 months (toddler stage). However, some Canadian patients who had received Men-ACWY only at 2 and 4 months were, at 12 months, given an unconjugated Men-ACWY vaccine.

Compared to measurements taken at 5 months of age, SBA geometric mean titers had declined by 12 months of age but were successfully increased by a 12-month dose of conjugated Men-ACWY. The %s of toddlers with SBA titers greater than or equal to 1:4 at 13 months of age were as follows:

| Country | Infant doses (months) | % SBA ≥ 1:4 (95% CI) | | | |
|---|---|---|---|---|---|
| | | A | C | W | Y |
| UK | 2/3/4 | 94 (84-98) | 98 (92-100) | 100 (94-100) | 100 (94-100) |
| UK | 2/4 | 86 (75-93) | 96 (87-99) | 100 (94-100) | 100 (95-100) |
| Canada | 2/4 | 92 (79-98) | 98 (87-100) | 100 (90-100) | 100 (91-100) |

Similar results were obtained if data were analyzed by multiple imputation analysis. Thus the 2/3/4-12 and 2/4-12 month schedules are both effective for raising bactericidal immune responses in children.

The 2/4-12 schedule was performed in Canada with either a conjugated Men-ACWY dose at 12 months or an unconjugated Men-ACWY dose. The effect of this different vaccine at 12 months can be seen by comparing at 13 months both (i) the % of participants with SBA titer ≥1:4 and (ii) SBA geometric mean titers. Values, showing 95% confidence intervals in brackets, were as follows:

| Measure | 12 month vaccine | A | C | W | Y |
|---|---|---|---|---|---|
| % SBA ≥ 1:4 | Conjugated | 92 (79-98) | 98 (87-100) | 100 (90-100) | 100 (91-100) |
| | Unconjugated | 78 (62-89) | 95 (83-99) | 98 (87-100) | 98 (87-100) |
| GMT | Conjugated | 67 (43-106) | 216 (130-356) | 381 (224-650) | 308 (191-499) |
| | Unconjugated | 28 (16-48) | 142 (80-254) | 367 (197-683) | 280 (175-447) |

Thus in all cases the conjugated vaccine was more effective as the 12 month dose.

It will be understood that the invention has been described by way of example only, and that modifications may be made whilst remaining within the scope and spirit of the invention.

REFERENCES

[1] Costantino et al. (1992) *Vaccine* 10:691-8.
[2] Lieberman et al. (1996) *JAMA* 275:1499-503.
[3] WO02/080965.
[4] WO02/058737.
[5] WO03/007985.
[6] Rennels et al. (2002) *Pediatr Infect Dis J* 21:978-979.
[7] Keyserling et al. (2005) *Arch Pediatr Adolesc Med* 159(10):907-13.
[8] Campbell et al. (2002) *J Infect Dis* 186:1848-1851.
[9] Vaccines. (eds. Plotkin & Orenstein). 4th edition, 2004, ISBN: 0-7216-9688-0.
[10] Trotter et al. (2004) *Lancet* 364:365-7.
[11] WO2005/000345.
[12] Twumasi et al. (1995) *J Infect Dis* 171:632-8.
[13] WO2005/105140
[14] Granoff et al. (2005) *Pediatr Infect Dis J* 24:132-6.
[15] Granoff & Harris (2004) *Pediatr Infect Dis J* 23:490-7.
[16] Granoff et al. (2005) *Vaccine* 23:4307-14.
[17] WO2004/103400.
[18] Anderson et al. (1994) *Infect Immun* 62:3391-5.
[19] WO02/00249.
[20] WO98/58670.
[21] WO98/58670.
[22] WO03/080678.
[23] Glode et al. (1979) *J Infect Dis* 139:52-56
[24] WO94/05325; U.S. Pat. No. 5,425,946.
[25] Arakere & Frasch (1991) *Infect. Immun.* 59:4349-4356.
[26] Michon et al. (2000) *Dev. Biol.* 103:151-160.
[27] Rubinstein & Stein (1998) *J. Immunol.* 141:4357-4362.
[28] WO2005/033148
[29] WO2007/000314.
[30] U.S. Pat. No. 4,709,017.
[31] WO93/25210.
[32] U.S. Pat. No. 5,917,017.
[33] WO00/48638.
[34] Del Guidice et al. (1998) *Molecular Aspects of Medicine* 19:1-70.
[35] Anonymous (January 2002) *Research Disclosure*, 453077.
[36] Anderson (1983) *Infect Immun* 39(1):233-238.
[37] Anderson et al. (1985) *J Clin Invest* 76(1):52-59.
[38] EP-A-0372501.
[39] EP-A-0378881.
[40] EP-A-0427347.
[41] WO93/17712
[42] WO94/03208.

[43] WO98/58668.
[44] EP-A-0471177.
[45] WO91/01146
[46] Falugi et al. (2001) *Eur J Immunol* 31:3816-3824.
[47] Baraldo et al. (2004) *Infect Immun* 72(8):4884-7.
[48] EP-A-0594610.
[49] Ruan et al. (1990) *J Immunol* 145:3379-3384.
[50] WO00/56360.
[51] Kuo et al. (1995) *Infect Immun* 63:2706-13.
[52] Michon et al. (1998) *Vaccine.* 16:1732-41.
[53] WO02/091998.
[54] WO01/72337
[55] WO00/61761.
[56] WO00/33882
[57] WO99/42130
[58] U.S. Pat. No. 4,711,779.
[59] WO2007/000341.
[60] *Mol. Immunol.,* 1985, 22, 907-919
[61] EP-A-0208375
[62] Bethell et al. (1979) *J. Biol. Chem.,* 254, 2572-4
[63] Hearn (1981) *J. Chromatogr.,* 218:509-18
[64] WO00/10599
[65] Gever et al., Med. Microbiol. Immunol, 165: 171-288 (1979).
[66] U.S. Pat. No. 4,057,685.
[67] U.S. Pat. Nos. 4,673,574; 4,761,283; 4,808,700.
[68] U.S. Pat. No. 4,459,286.
[69] U.S. Pat. No. 5,204,098
[70] U.S. Pat. No. 4,965,338
[71] U.S. Pat. No. 4,663,160.
[72] WO2007/000343.
[73] U.S. Pat. No. 4,761,283
[74] U.S. Pat. No. 4,356,170
[75] WO2007/000342.
[76] Lees et al. (1996) *Vaccine* 14:190-198.
[77] WO95/08348.
[78] WO98/42721.
[79] *W.H.O. Tech. Rep. Ser.* 594:51, 1976.
[80] WO2007/000322.
[81] Gennaro (2000) *Remington: The Science and Practice of Pharmacy.* 20th ed. ISBN: 0683306472.
[82] Nony et al. (2001) *Vaccine* 27:3645-51.
[83] Bardotti et al. (2008) *Vaccine* 25:2284-96.
[84] *Vaccine Design: The Subunit and Adjuvant Approach* (eds. Powell & Newman) 1995 (ISBN 0-306-44867-X).
[85] Snape et al. (2008) *JAMA* 299:173-84.

What is claimed is:

1. A method of immunising a human patient, comprising: (a) administering a multivalent meningococcal capsular saccharide-carrier protein conjugate vaccine to the patient at 2 to 4 months of age and (b) administering the multivalent meningococcal capsular saccharide-carrier protein conjugate vaccine to the patient when said patient is about 12 months of age, wherein the multivalent meningococcal capsular saccharide-carrier protein conjugate vaccine comprises capsular saccharide-carrier protein conjugates of meningococcal serogroups A, C, W135 and Y and wherein the average molecular weight of each of the capsular saccharides is <100 kDa.

2. The method of claim 1, wherein the carrier protein is selected from the group consisting of diphtheria toxoid, tetanus toxoid and CRM197.

3. The method of claim 1, wherein the multivalent meningococcal capsular saccharide-carrier protein conjugate vaccine is unadjuvanted.

4. A method of immunising a human patient who previously received a multivalent meningococcal capsular saccharide-carrier protein conjugate vaccine comprising capsular saccharide-carrier protein conjugates of meningococcal serogroups A, C, W135 and Y when the patient was aged 2 to 4 months, by administering the multivalent meningococcal capsular saccharide-carrier protein conjugate vaccine to the patient when the patient is aged about 12 months and wherein the average molecular weight of each of the capsular saccharides is <100 kDa.

5. The method of claim 1, wherein the first dose is administered at 2 months of age.

6. The method of claim 1, wherein the first dose is administered at 4 months of age.

* * * * *